US010130453B2

United States Patent
Winter

(10) Patent No.: US 10,130,453 B2
(45) Date of Patent: Nov. 20, 2018

(54) BITE REGISTRATION DEVICE

(71) Applicant: Daniel M. Winter, Manhattan, KS (US)

(72) Inventor: Daniel M. Winter, Manhattan, KS (US)

( * ) Notice: Subject to any disclaimer, the term of this patent is extended or adjusted under 35 U.S.C. 154(b) by 0 days.

(21) Appl. No.: 15/718,365

(22) Filed: Sep. 28, 2017

(65) Prior Publication Data

US 2018/0085208 A1 Mar. 29, 2018

Related U.S. Application Data

(60) Provisional application No. 62/400,995, filed on Sep. 28, 2016.

(51) Int. Cl.
*A61C 9/00* (2006.01)
*A61C 19/05* (2006.01)

(52) U.S. Cl.
CPC ............ *A61C 19/05* (2013.01); *A61C 9/0006* (2013.01)

(58) Field of Classification Search
CPC ....... A61C 9/00; A61C 9/0006; A61C 9/0013; A61C 9/0026; A61C 9/0063; A61C 19/05; A61C 13/081
USPC .................................................. 433/37, 214
See application file for complete search history.

(56) References Cited

U.S. PATENT DOCUMENTS

| 3,890,711 | A | 6/1975 | Burns |
| 4,382,785 | A | 5/1983 | Lococo |
| 7,871,269 | B2 | 1/2011 | Wu et al. |

FOREIGN PATENT DOCUMENTS

| DE | 202006001141 | 7/2007 |
| WO | 2017048918 | 3/2017 |

OTHER PUBLICATIONS

International Search Report and Written Opinion dated Nov. 28, 2017, in PCT/US2017/053937 filed Sep. 28, 2017.

*Primary Examiner* — Yogesh Patel
*Assistant Examiner* — Matthew Saunders
(74) *Attorney, Agent, or Firm* — Hovey Williams LLP

(57) ABSTRACT

A bite registration device is provided that can be placed within a patient's mouth and adjusted to a desired position relative to the patient's maxillary and/or mandibular teeth while permitting visual inspection of the patient's anterior teeth during acquisition of the bite registration. The bite registration device is also configured to permit introduction of bite registration material without having to remove the device from the patient's mouth once optimal positioning has been established.

15 Claims, 5 Drawing Sheets

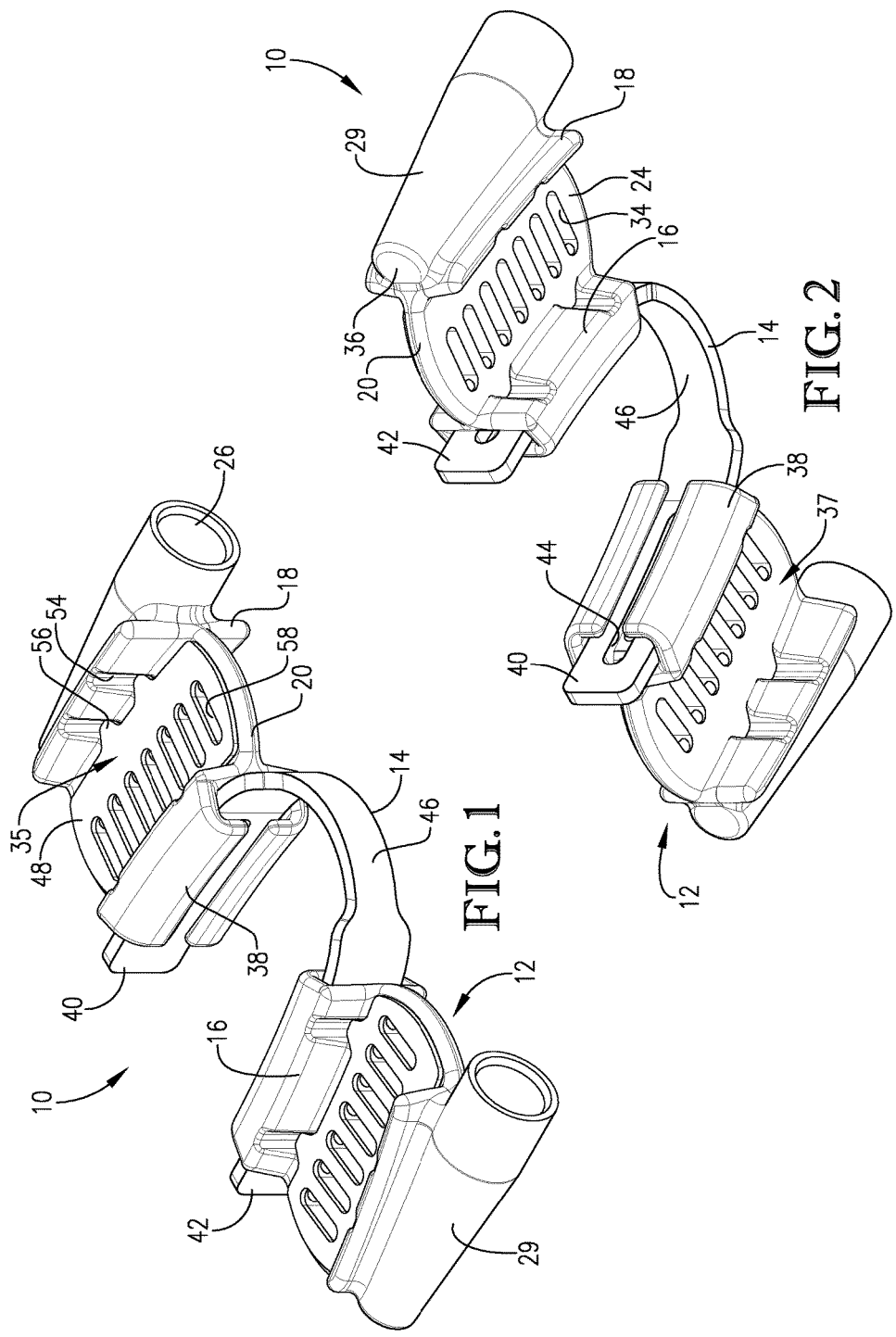

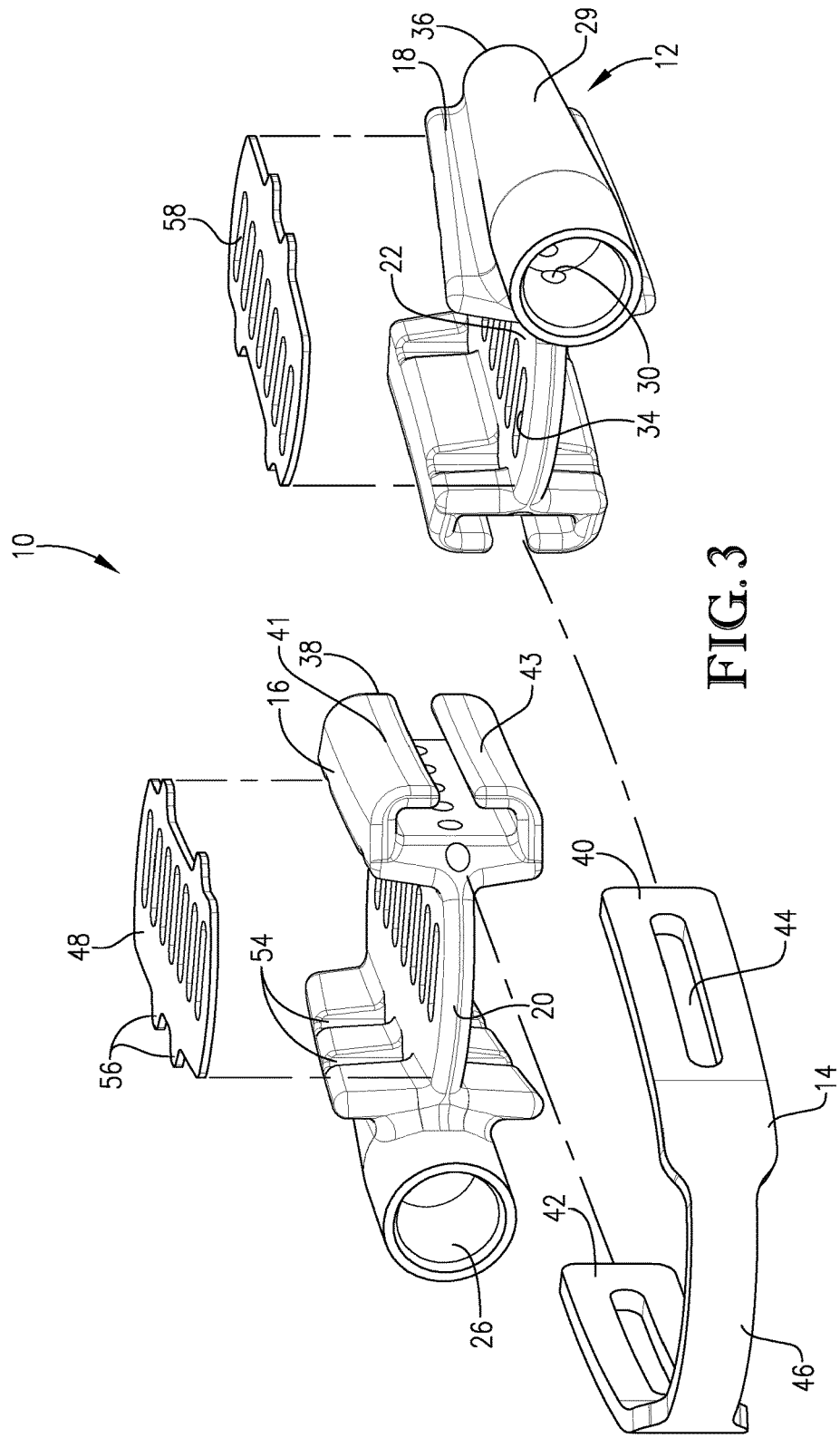

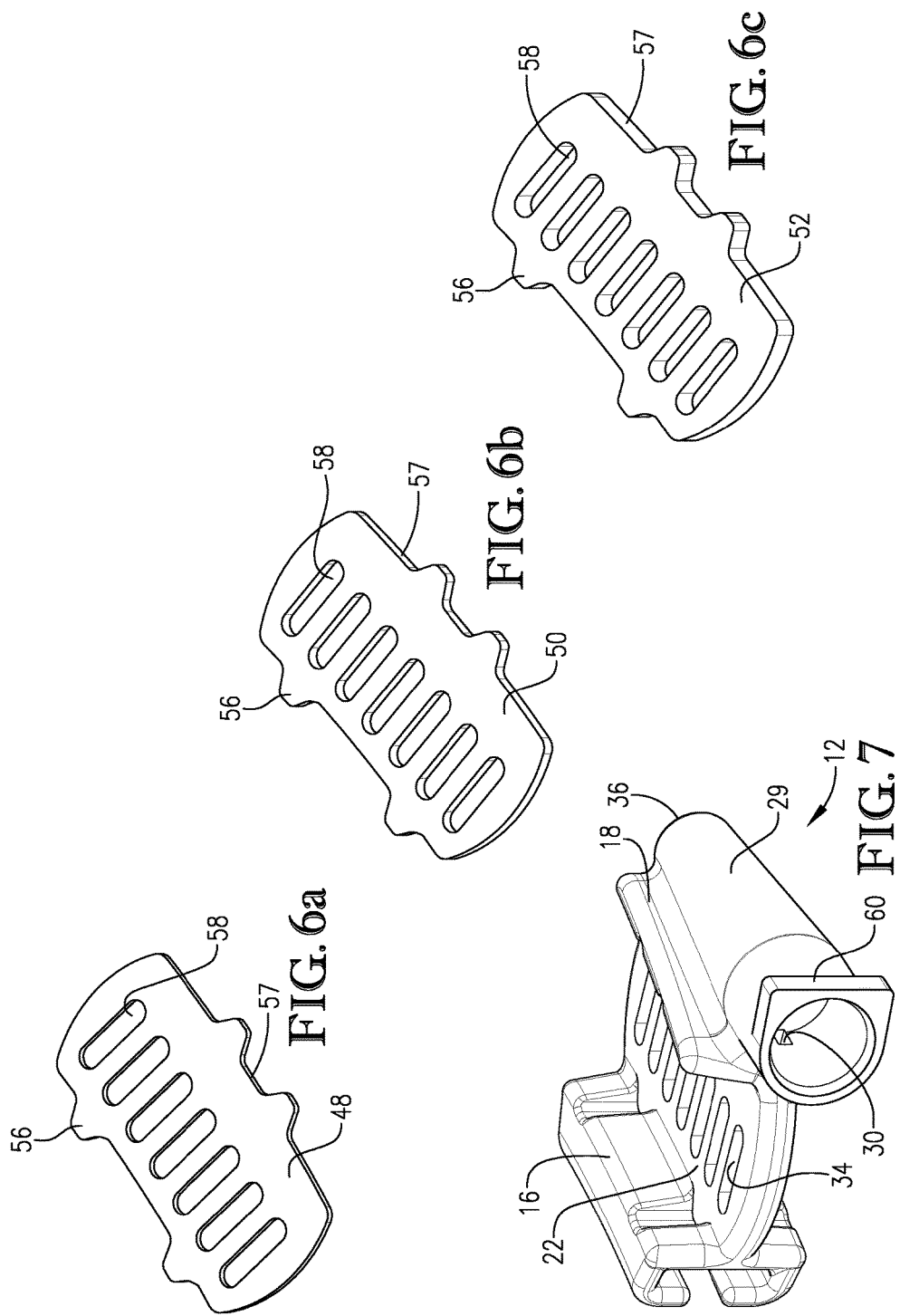

BITE REGISTRATION DEVICE

CROSS-REFERENCE TO RELATED APPLICATION

This application claims the benefit of U.S. Provisional Patent Application No. 62/400,995, filed Sep. 28, 2016, which is incorporated by reference herein in its entirety.

BACKGROUND OF THE INVENTION

Field of the Invention

The present invention is generally directed toward a device for taking bite registrations in which the device can be placed within a patient's mouth, adjusted to a desired position relative to the patient's maxillary and/or mandibular teeth, and bite registration material can be introduced without having to remove the device from the patient's mouth.

Description of the Prior Art

Mandibular repositioning devices, otherwise known as oral appliances, are designed to hold an individual's lower jaw downward and/or forward during sleep to improve airflow and reduce the impact of sleep apnea and/or other related sleep breathing disorders in individuals. For these devices to be effective, each oral appliance must be custom fit to the individual so that the lower jaw is moved to an optimal location to maximize the patient's airflow.

A trained dentist through proper assessment is able to determine the potential clinical efficacy of oral appliance therapy for sleep discorded breathing. This assessment should include a complete oropharyngeal examination with a goal of determining the optimal maxillary-mandibular position to treat the patient's symptoms. This relationship of the maxilla and mandible can be referred to as the optimal mandibular position. This position must be captured or recorded with complete accuracy utilizing a bite registration.

Once the dentist has determined that the mandibular position provided by the oral appliance will meet the needs of the patient, it is his or her responsibility to measure the patient and provide the oral appliance manufacturer with the accurate registration needed to make the device meet the patient's needs. To accomplish this, the dentists will capture impressions of the upper and lower dental arches utilizing techniques taught and practiced uniformly within the field of dentistry. The dentist is also responsible for capturing and recording the relationship between the upper and lower teeth or jaws of the patient. For the treatment of sleep-disordered breathing with oral appliances, the technique utilized in capturing an accurate relationship between the upper and lower teeth is critical. This is known as the bite registration.

There are many products available to aid in measured adjustment and recording of the bite registration of a patient's upper and lower teeth and/or jaw. These tools can be used for the vertical adjustment of the jaw with respect to the upper and lower jaw as well as horizontal adjustment; however, none also aid in recording the bite registration simultaneously.

Positioning aids are tools that are used to adjust the patient's jaw so that the dentist is able to determine the optimal position where the patient's mandible is in its best possible position to maximize airflow. Once this position is defined, it is critical to obtain a bite registration to document or record the upper and lower jaw relationship. This is typically done through the use of a two-part bite registration material that upon mixing cures relatively quickly, easily releases from the teeth, and remains dimensionally stable once cured. One exemplary bite registration material is polyvinyl siloxane (PVS).

The problem with this process is that many of the tools presently available help adjust a patient's jaw in several directions so that the dentist can determine best possible options; however, these tools must then be removed from the patient's mouth to apply the bite registration material. Once the registration tools have been removed from the mouth, the dentist loses "exact" measurement that he or she had determined previously to be optimal. Once the bite registration material is applied and reinserted into the patient's mouth, the dentist attempts to reposition the patient's jaw in the same location previously identified. Many of these tools or aids require the patient to rest his/her front teeth into a rest or receiver located on the tool. This does not allow the dentist to visually verify the exact position the teeth were in prior to the tools removal to apply bite registration material.

Dental impression trays are available with the capability to deliver dental impression material around the teeth while remaining in the mouth. No bite registration tray/aid/tool exists with the capability of delivering bite registration material to the teeth and thus capturing a bite registration without removing the tray/aid/tool from the patient's mouth. Moreover, conventional devices tend to obscure the patient's anterior teeth during use so that the dentist is unable to assess mandibular position through direct visual inspection.

SUMMARY OF THE INVENTION

The present invention overcomes the aforementioned problems by providing a device for taking bite registrations and methods of using such a tool. According to one embodiment of the present invention, the device comprises a pair of side bodies configured to maintain a separation between opposed maxillary and mandibular teeth and a strap connecting the side bodies. At least one of the side bodies comprises a lingual sidewall structure, a buccal sidewall structure, and an occlusal wall structure interconnecting the lingual and buccal sidewall structures. The occlusal wall structure comprises opposed maxillary and mandibular bite surfaces. At least one of the side bodies comprises a port that is configured to be coupled with a source of bite registration material and to direct bite registration material received through the port into a chamber. The buccal sidewall structure comprises one or more orifices that permit communication between the chamber and one or more respective passages formed within the occlusal wall structure. The occlusal wall structure comprises one or more openings formed therein that permit communication between at least one of the passages and the maxillary and/or mandibular bite surfaces.

According to another embodiment of the present invention, the device comprises a pair of side bodies configured to maintain a separation between opposed maxillary and mandibular teeth. Each of the side bodies comprises a lingual sidewall structure, a buccal sidewall structure, and an occlusal wall structure interconnecting the lingual and buccal sidewall structures. The occlusal structure comprises opposed maxillary and mandibular bite surfaces. Each of the side bodies comprises a port that is configured to be coupled with a source of bite registration material and to direct bite registration material received through the port into a chamber that is defined at least in part by the buccal sidewall structure. The buccal sidewall structure comprises a plurality of orifices that permit communication between the chamber and a plurality of respective passages formed within the occlusal wall structure. The occlusal wall structure comprises one or more openings formed therein that permit communication between at least one of the passages and the maxillary and/or mandibular bite surfaces. The device further comprises a strap connecting the side bodies, wherein the strap is slidably received within respective attachment guides formed within the lingual sidewall structure of each of the side bodies.

According to yet another embodiment of the present invention, there is provided a method of taking a bite registration. A device made in accordance with the present invention as described and illustrated herein in inserted within the mouth of a patient. The relative positioning of the side bodies relative to at least some of the patient's maxillary and mandibular teeth is adjusted. A bite registration material is injected through the port of at least one of the side bodies thereby causing the bite registration material to flow into the chamber, into the passages, out of the one or more openings formed in the occlusal wall structure, and around one or more of the patient's maxillary and/or mandibular teeth.

BRIEF DESCRIPTION OF THE DRAWINGS

FIG. 1 is an assembled, upper-perspective view of a device for taking a bite registration according to one embodiment of the present invention;

FIG. 2 is an assembled, lower-perspective view of the device of FIG. 1;

FIG. 3 is an expanded view of the device of FIG. 1;

FIGS. 6a, 6b, and 6c are perspective views of shims of varying thicknesses that can be used with the device of FIG. 1; and FIG. 7 illustrates an alternate embodiment of a side body that may be used with a bite registration device of the present invention.

DETAILED DESCRIPTION OF THE PREFERRED EMBODIMENT

In order to maximize the effectiveness of taking a patient's bite registration, the dentist needs the ability to adjust the patient's lower jaw to the optimal location and then take a bite registration of that location without having to move the lower jaw in any manner. In order to accomplish this, the present invention pertains to a bite registration device 10 that enables jaw manipulation to occur while at the same time permitting the dentist to apply bite registration without having to remove the device 10 from the patient's mouth. Device 10 also provides the dentist with a full visual appreciation of the patient's anterior teeth and their relationship to each other during the bite acquisition process.

Turning to FIGS. 1-5, device 10 comprises a pair of side bodies 12 configured to maintain a separation between the occlusal surfaces of opposed maxillary and mandibular teeth. Device 10 further comprises a strap 14 that interconnects the side bodies 12. In certain embodiments side bodies 12 are of identical construction and merely oriented in a mirror image fashion when being secured together via strap 14; however, this need not always be the case, as side bodies 12 can be configured differently, if desired.

Figure 4:
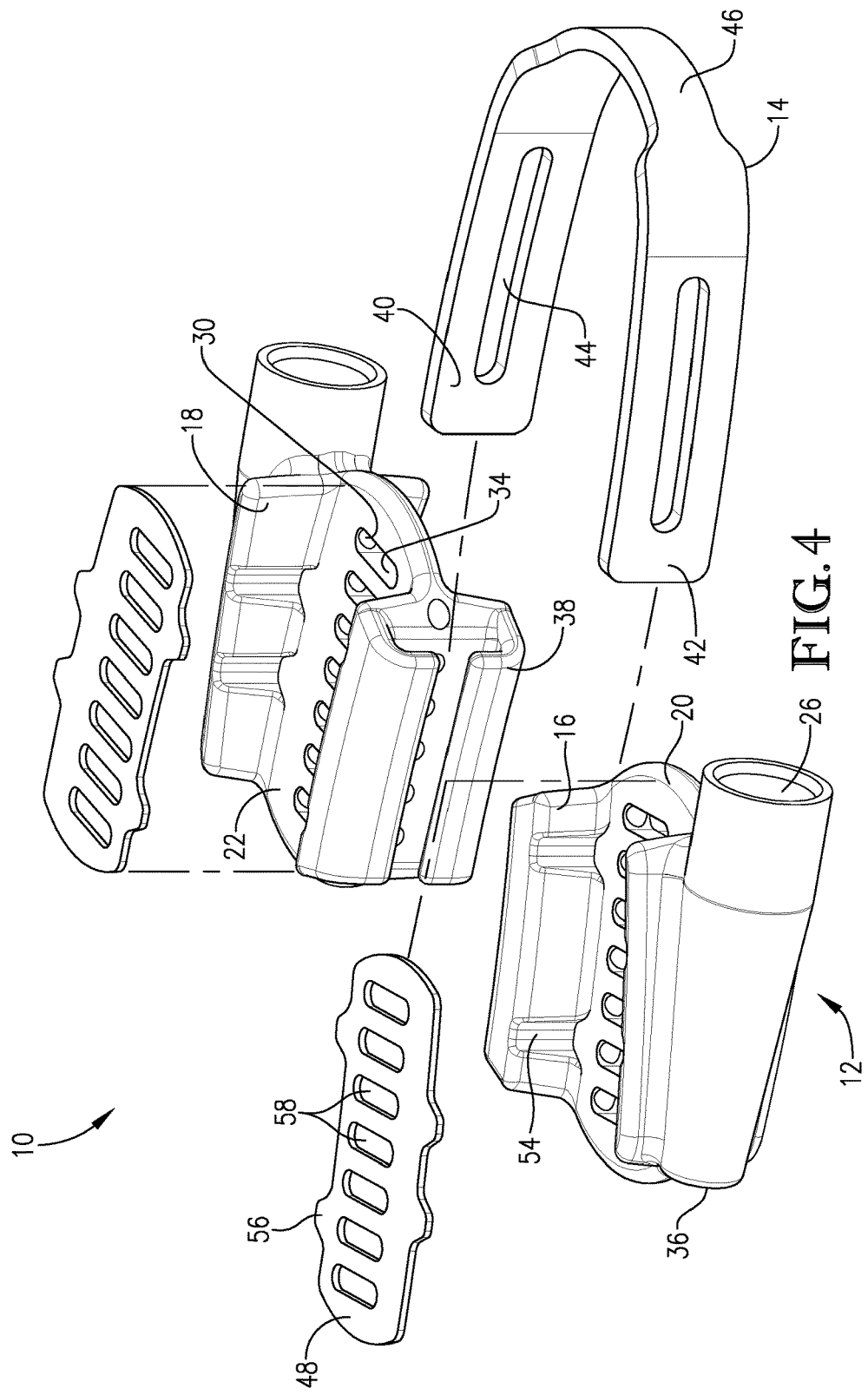
FIG. 4 is an expanded, side-perspective view of the device of FIG. 1
Figure 5:
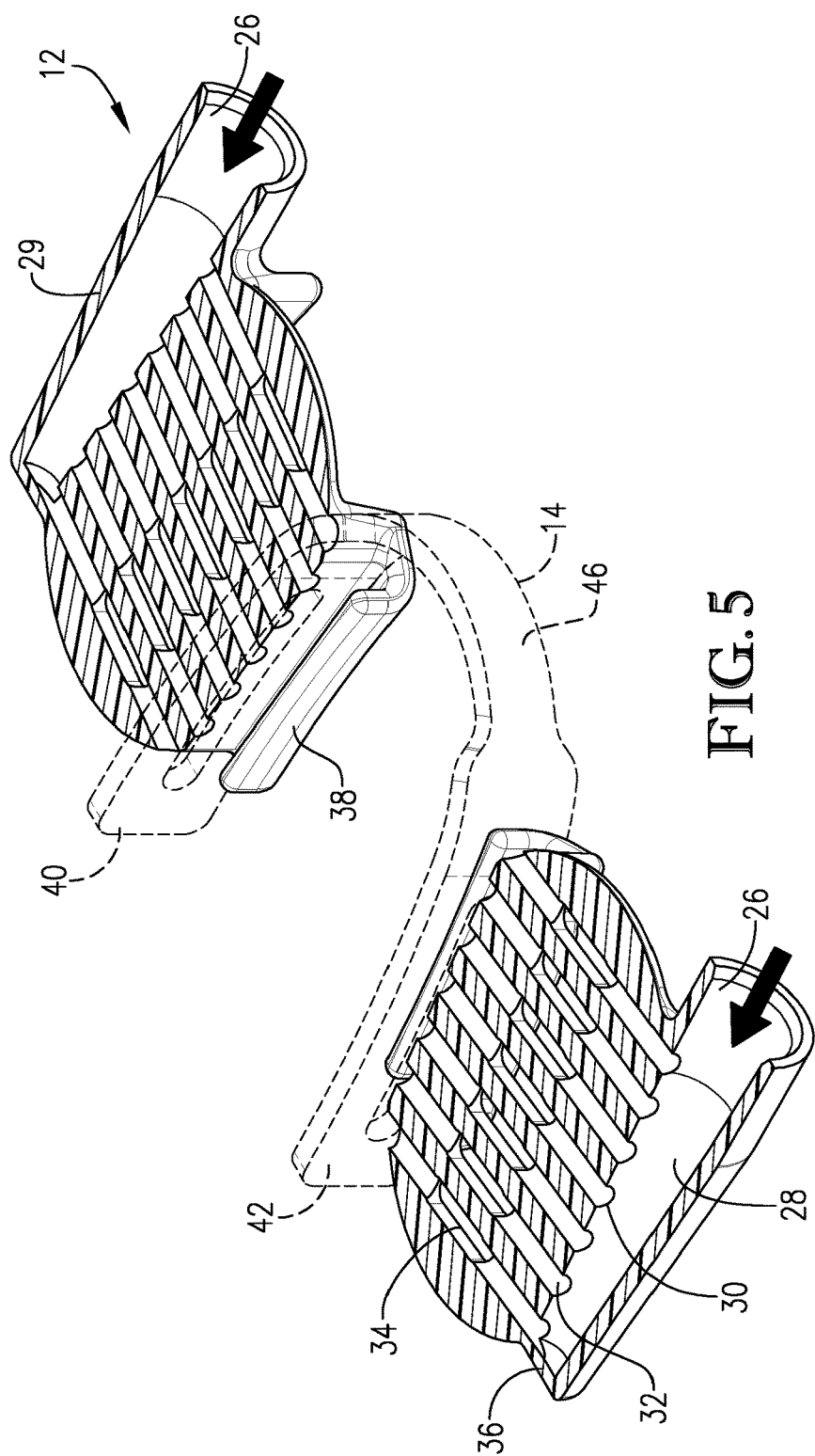
FIG. 5 is a sectioned view of the side bodies of the device of FIG. 1.

Side body 12 comprises a lingual sidewall structure 16, a buccal sidewall structure 18, and an occlusal wall structure 20 that extends between and interconnects the lingual and buccal sidewall structures 16, 18. The occlusal wall structure 20 comprises opposed maxillary 22 and mandibular 24 bite surfaces. Side body 12 comprises a port 26 that is configured to be coupled with a source of bite registration material (not shown). Generally, bite registration material may be supplied in the form of a tube or gun having a nozzle that is configured to be inserted into port 26 or otherwise attached thereto. As shown in FIG. 5, port 26 communicates with a chamber 28 that is defined, at least in part, by and/or attached to buccal sidewall structure 18. In certain embodiments, chamber 28 and the portion 29 of buccal sidewall structure 18 by which it is defined are frustoconical. Port 26 faces the anterior portion of the patient's mouth, and may extend outside the patient's mouth, when device 10 is placed within the patient's mouth, and directs bite registration material received therethrough into chamber 28.

Buccal sidewall structure 18 further includes one or more orifices 30 that permit communication between the chamber 28 and one or more respective passages 32 formed within the occlusal wall structure 20. Chamber 28 comprises a closed end 36 located opposite port 26 that forces bite registration material directed through port 26 to flow through orifices 30 and into passages 32. The occlusal wall structure 20 comprises one or more openings 34 formed therein that permit communication between at least one of the passages 32 and the maxillary 22 and/or mandibular 24 bite surfaces. Thus, when bite registration material is introduced through port 26, the material flows out of openings 34 and occupies the space 35 that is defined between lingual 16 and buccal 18 sidewall structures and the maxillary bite surface 22, and/or the space 37 that is defined between lingual 16 and buccal 18 sidewall structures and the mandibular bite surface 24. Generally, during introduction of the bite registration material, device 10 is located within the patient's mouth and several of the patient's teeth, especially the patient's first and second molars, and possibly the patient's first and second bicuspids, are also located within spaces 35 and 37. Therefore, the bite registration material will flow around the patient's teeth within spaces 35 and 37.

Lingual sidewall structure 16 comprises an attachment guide 38 through which a band or strap 14 is slidably received. Strap 14 functions to maintain a desired relative positioning between the pair of side bodies 12 during use of device 10. Strap 14 comprises opposed end section 40, 42 that are interconnected by a medial section 46. End sections 40, 42 are configured to be received within attachment guide 38 and maintained by guards 41, 43. The anterior reach of medial section 46 may be adjusted by sliding end sections 40, 42 within attachment guide 38. In certain embodiments, strap 14 is configured with slots 44 formed in each of strap end sections 40, 42. These slots 44 are configured to receive bite registration material that flows through passages 32, across openings 34, and through the lingual sidewall structure. However, in alternate embodiments, passages 32 can be configured to terminate prior to lingual sidewall structure 16, such as at openings 34, which would eliminate the need for slots 44.

As can be seen, at least a portion of medial section 46 has a width that is less than the width of at least one of end sections 40, 42. This tapering of medial section 46 assures a comfortable fit of device 10, and in particular strap 14, across the patient's anterior teeth and/or gums. Importantly, too, the tapering of medial section 46, and the general configuration of device 10, ensures that the dentist is capable of visually inspecting at least some of the patient's maxillary and mandibular teeth and their relationship to each other during bite registration acquisition.

In certain embodiments, device 10 may be configured to accommodate one or more removable shims 48 that are placed into contact with at least one of the maxillary 22 and mandibular 24 bite surfaces and are capable of adjusting the vertical relationship between the maxilla and mandible. Shims 48 are configured to increase the separation between opposed maxillary and mandibular teeth thereby allowing the dentist flexibility to vary the vertical dimension independently from one side to the other as needed.

The upper portion has a feature which accepts removable shims capable of adjusting the vertical relationship of the upper and lower jaw. Shim installation can be in any manner necessary to appropriately space the jaws to the correct proportion. This allows the dentist flexibility to vary the vertical dimension independently from one side to another if needed. As can be seen in FIGS. 6a, 6b, and 6c, shims 48, 50, 52, respectively, can be provided in a variety of thicknesses. In certain embodiments, the thicknesses of the shims can be provided in 0.5 mm increments (i.e., shim 48 having a thickness of 0.5 mm, shim 50 having a thickness of 1.0 mm, and shim 52 having a thickness of 1.5 mm) allowing for any desired thickness between posterior teeth. The shims can be stacked upon each other to increase spacing.

Shims 48, 50, 52 can be provided with a plurality of securement structures or tabs 56 that extend outwardly from a circumscribing shim sidewall surface 57 and that are configured to mate with the corresponding sidewall guides 54 formed in the lingual 16 and buccal 18 sidewall structures. Tabs 56 are configured to restrain lateral movement of the shims when installed within device 10. As illustrated, the spacing between proximal tabs 57 can be varied from one side of the shim to the other. This ensures proper orientation of shims 48, 50, 52 when added to device 10.

Shims 48, 50, 52 comprise at least one opening 58 formed therein that are configured to be in registry with the one or more openings 34 formed in the occlusal wall structure 20 when the shims are installed within device 10. While openings 58 are shown to have an essentially identical configuration to openings 34 in the occlusal wall structure 34, this need not always be the case and openings 58 need only be configured to direct bite registration material flowing through openings 34 into spaces 35 and 37.

When being used to take a bite registration, the dentist inserts device 10 into the patient's mouth and adjusts the positioning of side bodies 12 relative to at least some of the patient's maxillary and mandibular teeth. The relative positioning may occur, for example, by having the patient move his or her mandible forward and/or adding shims 48 to either or both of the maxillary 22 and mandibular 24 bite surfaces. The device 10 may need to be removed from the patient's mouth in order to add any necessary shims 48. However, once the dentist has set the relative positioning, the device 10 is not removed from the patient's mouth until after the bite registration has been taken.

A major drawback associated with conventional bite registration devices is that they capture all teeth within a patient's mouth, and therefore, cover many or all of the patient's teeth in the process. This impedes the dentist's ability to visually inspect the patient's teeth during bite registration acquisition. As noted previously, device 10 is configured so as to permit the dentist to be able to inspect visually at least some of the patient's maxillary and mandibular teeth and their relationship to each other during bite registration acquisition. Device 10 is configured so that the patient's anterior teeth remain relatively unobstructed, except for the presence of strap 14, so that the dentist can visually appreciate the patient's teeth throughout the acquisition process and make appropriate adjustments to the patient in order to maximize oral appliance benefit.

Once the dentist has identified the appropriate bite registration between the patient's mandibular and maxillary teeth, the recording of the registration is carried out by injecting a bite registration material through a port 26 of at least one of the side bodies 12. In certain embodiments, the dentist begins by attaching a source of bite registration material to port 26 of one of side bodies 12, and once sufficient material has been introduced, the source is disconnected and the dentist repeats this operation with respect to the other of side bodies 12. The dentist causes the bite registration material to flow into the chamber 28, into the passages 32, out of the one or more openings 34 formed in the occlusal wall structure 20 (and any shim openings 58, if present). The bite registration material enters into spaces 35 and 37 and flows around one or more of the patient's maxillary and/or mandibular teeth.

The bite registration material is permitted to cure around the one or more of the patient's maxillary and/or mandibular teeth. Following curing of the bite registration material, the device is removed from the patient's mouth, and the recorded bite registration is ready to be used in the manufacture of a dental appliance.

FIG. 7 illustrates an alternate embodiment of a side body 12 that may be used to construct a device 10 according to the present invention. Generally, body 12 of FIG. 7 is substantially the same as side body 12 illustrated in FIGS. 1-5. However, body 12 further comprises a flange 60 that extends laterally from the outer, lingually-oriented portion of port 26. This flange permits side body 12 to be grasped while the device 10 is inserted into the patient's mouth, particularly when the source of bite registration material (not shown) is attached to port 26. Upon inserting the tubing through which the bite registration material is delivered to device 10 into port 26, the force associated therewith may inadvertently cause the device 10 and/or the patient's mandible to shift. Being able to grasp and stabilize the device 10 during delivery of the bite registration material prevents such inadvertent shifting giving the dentist greater control and assurance of recording the optimal bite registration. As an alternative to flange 60, other structures or surfaces may be provided on side body 12 and/or strap 14 to allow the dentist to grasp device 10 once inside the patient's mouth. For example, a button, tab, slot, or other structure may be provided on a portion of device 10 that is configured to be coupled to a handle or other tool so that shifting of device 10 or the patient's mandible during delivery of the bite registration material can be avoided.

It is understood that the aforementioned description is illustrative of the present invention and should not be taken as limiting upon the overall scope of the invention. It is also understood that not all structures shown in the Figures and described herein are necessary for the successful practice of the present invention, but rather represent those features that may be found within a preferred embodiment of the present invention.

I claim:

1. A device for taking a bite registration of a patient comprising:
   a pair of side bodies configured to maintain a separation between opposed maxillary and mandibular teeth; and
   a strap connecting the side bodies,
   at least one of the side bodies comprises a lingual sidewall structure, a buccal sidewall structure, and an occlusal wall structure interconnecting the lingual and buccal sidewall structures, the occlusal wall structure comprising opposed maxillary and mandibular bite surfaces, at least one of the side bodies comprises a port that is configured to be coupled with a source of bite registration material and to direct bite registration material received through the port into a chamber, the buccal sidewall structure comprising one or more orifices that permit communication between the chamber and one or more respective passages formed within the occlusal wall structure, the occlusal wall structure comprising one or more openings formed therein that permit communication between at least one of the passages and the maxillary and/or mandibular bite surfaces.

2. The device according to claim 1, wherein the chamber is frustoconical and has a closed end located opposite of the port.

3. The device according to claim 1, wherein the lingual sidewall structure comprises an attachment guide through which the strap is slidably received.

4. The device according to claim 3, wherein the strap comprises opposed end sections, at least one end section comprises an elongated slot, at least a portion of each end section being received within the attachment guide.

5. The device according to claim 4, wherein the strap comprises a medial section interconnecting the opposed end sections, the medial section having a width that is less than the width of at least one of the end sections.

6. The device according to claim 1, wherein the chamber is attached to the buccal sidewall structure, and wherein the port faces the anterior portion of the patient's mouth when the device is placed in the patient's mouth.

7. The device according to claim 1, wherein the device further comprises one or more shims that are placed into contact with at least one of the maxillary and mandibular bite surfaces, the shims being configured to increase the separation between opposed maxillary and mandibular teeth.

8. The device according to claim 7, wherein the lingual sidewall structure and the buccal sidewall structure each comprise one or more guides configured to mate with corresponding securement structures formed in the one or more shims so as to restrain lateral movement of the one or more shims when installed within the device.

9. The device according to claim 7, wherein the one or more shims comprise one or more openings that are in registry with the one or more openings formed in the occlusal wall structure when the one or more shims are installed within the device.

10. The device according to claim 1, wherein the device is configured to permit visual inspection of at least some of the patient's maxillary and mandibular teeth and their relationship to each other during bite registration acquisition.

11. A device for taking a bite registration of a patient comprising:

a pair of side bodies configured to maintain a separation between opposed maxillary and mandibular teeth, wherein each of the side bodies comprises a lingual sidewall structure, a buccal sidewall structure, and an occlusal wall structure interconnecting the lingual and buccal sidewall structures, the occlusal structure comprising opposed maxillary and mandibular bite surfaces, wherein each of the side bodies comprises a port that is configured to be coupled with a source of bite registration material and to direct bite registration material received through the port into a chamber that is defined at least in part by the buccal sidewall structure, wherein the buccal sidewall structure comprises a plurality of orifices that permit communication between the chamber and a plurality of respective passages formed within the occlusal wall structure, wherein the occlusal wall structure comprises one or more openings formed therein that permit communication between at least one of the passages and the maxillary and/or mandibular bite surfaces; and a strap connecting the side bodies, wherein the strap is slidably received within respective attachment guides formed within the lingual sidewall structure of each of the side bodies.

12. A method of taking a bite registration of a patient comprising:

inserting within the mouth of the patient the device according to any of claim 1;

adjusting the relative positioning of the side bodies relative to at least some of the patient's maxillary and mandibular teeth; and injecting a bite registration material through the port of at least one of the side bodies thereby causing the bite registration material to flow into the chamber, into the passages, out of the one or more openings formed in the occlusal wall structure, and around one or more of the patient's maxillary and/or mandibular teeth.

13. The method according to claim 12, wherein the device is not removed from the patient's mouth in between the adjusting step and the injecting step.

14. The method according to claim 12, wherein the bite registration material is permitted to cure around the one or more of the patient's maxillary and/or mandibular teeth, and following curing of the bite registration material, the device is removed from the patient's mouth.

15. The method according to claim 12, wherein the device is configured to permit visual inspection of at least some of the patient's maxillary and mandibular teeth and their relationship to each other during bite registration acquisition.

* * * * *